United States Patent [19]

Spears et al.

[11] Patent Number: 5,693,017
[45] Date of Patent: Dec. 2, 1997

US005693017A

[54] APPARATUS AND METHOD OF DELIVERY OF GAS-SUPERSATURATED SOLUTIONS TO A DELIVERY SITE

[75] Inventors: James Richard Spears, Bloomfield Hills, Mich.; Richard James Crilly, Wondsor, Canada

[73] Assignee: Wayne State University, Detroit, Mich.

[21] Appl. No.: 484,279

[22] Filed: Jun. 7, 1995

Related U.S. Application Data

[63] Continuation-in-part of Ser. No. 353,137, Dec. 9, 1994, Pat. No. 5,599,296, which is a continuation-in-part of Ser. No. 273,652, Jul. 12, 1994, Pat. No. 5,569,180, which is a continuation-in-part of Ser. No. 152,589, Nov. 15, 1993, Pat. No. 5,407,426, which is a continuation-in-part of Ser. No. 818,045, Jan. 8, 1992, Pat. No. 5,261,875, which is a continuation of Ser. No. 655,078, Feb. 14, 1991, Pat. No. 5,086,620.

[51] Int. Cl.$^6$ .................................................. A61M 37/00
[52] U.S. Cl. .................. 604/132; 604/24; 604/26; 604/147; 222/22; 222/95; 222/400.7; 261/121.1
[58] Field of Search .................. 222/82, 95, 400.7, 222/146.2, 55; 261/121.1; 604/24.53, 49, 26, 52, 132, 140, 141, 147; 128/203.12, 203.16, 203.25

[56] References Cited

U.S. PATENT DOCUMENTS

| | | |
|---|---|---|
| 3,721,231 | 3/1973 | Hubert . |
| 3,743,145 | 7/1973 | Johnston .......................... 222/400.7 |
| 4,039,639 | 8/1977 | Kankel et al. ..................... 261/121.1 |
| 4,122,858 | 10/1978 | Schiff . |
| 4,196,726 | 4/1980 | Ronzi ................................ 604/24 X |
| 4,445,896 | 5/1984 | Gianturco . |
| 4,610,661 | 9/1986 | Possis et al. . |
| 4,770,168 | 9/1988 | Rusz et al. ........................ 128/203.12 |
| 4,834,719 | 5/1989 | Arenas . |
| 4,857,055 | 8/1989 | Wang ................................ 604/133 |
| 4,877,031 | 10/1989 | Conway et al. . |
| 5,021,044 | 6/1991 | Sharkawy . |
| 5,059,182 | 10/1991 | Laing .............................. 604/142 |
| 5,065,753 | 11/1991 | Kalishman ........................ 128/203.12 X |
| 5,084,011 | 1/1992 | Grady ............................... 604/24 |
| 5,114,423 | 5/1992 | Kasprzyk et al. . |
| 5,119,807 | 6/1992 | Roberts ............................ 128/203.12 |
| 5,124,088 | 6/1992 | Stumphauzer ...................... 261/121.1 |
| 5,137,513 | 8/1992 | McInnes et al. . |
| 5,158,540 | 10/1992 | Wijay et al. . |
| 5,180,364 | 1/1993 | Ginsburg . |
| 5,195,971 | 3/1993 | Sirhan . |
| 5,211,637 | 5/1993 | Goto et al. . |
| 5,226,888 | 7/1993 | Arney . |
| 5,252,159 | 10/1993 | Arney . |
| 5,273,052 | 12/1993 | Krans et al. . |
| 5,279,562 | 1/1994 | Sirhan et al. . |
| 5,292,030 | 3/1994 | Kateman et al. .................. 222/146.6 X |
| 5,334,142 | 8/1994 | Paradis . |
| 5,356,388 | 10/1994 | Sepetka et al. . |
| 5,368,195 | 11/1994 | Pleet et al. ....................... 222/95 X |
| 5,383,853 | 1/1995 | Jung et al. . |
| 5,413,558 | 5/1995 | Paradis . |
| 5,437,633 | 8/1995 | Manning . |
| 5,507,280 | 4/1996 | Henkin et al. .................... 128/203.12 |

OTHER PUBLICATIONS

"Use of Hyperbaric Oxygen as Oxygen Source in Extracorporeal Oxygenation of Blood", C. Boe, et al; Physiological and Clinical Aspects of Oxygenator Design, ed. by Dawids and Engell; publ. by Elsevier/North-Holland Biomedical Press, Luxembourg, 1976.

"Cavitation in Gas–Supersaturated Solutions", Edvard A. Hemmingsen; Journal of Applied Physics, vol. 46, No. 1, Jan. 1976.

"Supersaturated Fluorocarbon as an Oxygen Source", Pieter Stroev, et al; Physiological and Clinical Aspects of Oxygenator Design, ed. by Dawids and Engell; publ. by Elsevier/ North–Holland Biomedical Press, Luxembourg, 1976.

*Primary Examiner*—Michael Powell Buiz
*Assistant Examiner*—Chalin Smith
*Attorney, Agent, or Firm*—Brooks & Kushman P.C.

[57] ABSTRACT

An apparatus (10) and method for delivering an oxygen-supersaturated physiologic solution (12) into a lumen (14) of a blood vessel (16) to replace arterial blood beyond an angioplasty catheter (18) during clinical angioplasty without bubble formation.

32 Claims, 2 Drawing Sheets

APPARATUS AND METHOD OF DELIVERY OF GAS-SUPERSATURATED SOLUTIONS TO A DELIVERY SITE

CROSS REFERENCE TO RELATED APPLICATIONS

This application is a continuation-in-part of application Ser. No. 08/353,137, filed on Dec. 9, 1994, now U.S. Pat. No. 5,599,296, which is a continuation-in-part of application Ser. No. 08/273,652, filed Jul. 12, 1994, now U.S. Pat. No. 5,569,180, which is a continuation-in-part of application Ser. No. 08/152,589, filed Nov. 15, 1993 (now U.S. Pat. No. 5,407,426), which is a continuation-in-part of application Ser. No. 07/818,045, filed Jan. 8, 1992 (now U.S. Pat. No. 5,261,875), which is a continuation of application Ser. No. 07/655,078, filed Feb. 14, 1991 (now U.S. Pat. No. 5,086,620). The disclosures in each of the above-referenced cases are incorporated herein by reference.

TECHNICAL FIELD

This invention relates to an apparatus and method for delivering oxygen-supersaturated physiologic solutions during clinical procedures, such as angioplasty.

RELATED ART

I have previously disclosed methods for delivering oxygen-supersaturated solutions into blood without cavitation. Such solutions contain high levels of oxygen.

In clinical angioplasty, it would be desirable to replace arterial blood beyond an angioplasty device with a physiologic solution containing oxygen. However, when the oxygen is dissolved under pressures greater than about 1 bar, there is an increased risk of bubble formation which may lead to potential oxygen toxicity.

SUMMARY OF THE INVENTION

This invention relates to an apparatus and method for delivering oxygen-supersaturated physiologic solutions during angioplasty to replace arterial blood without bubble formation.

A collapsible container of a physiologic solution is disposed within a hollow, gas-tight vessel so that a space between the container and the vessel is created. A trocar is located within the container, the trocar being in communication with a supply of oxygen under pressure. The trocar drives the oxygen into solution to prepare the oxygen-supersaturated solution within the container.

An inlet port is provided in the vessel in communication with the space and the supply of oxygen for pressurizing the space. The supply is in simultaneous communication with the space external to the container within the vessel and with the physiologic solution.

To control the flow of undissolved oxygen from the space, an adjustable space exit valve is connected to the vessel. By adjustment, the exit valve permits a flow of oxygen from the space at a higher rate than that at which oxygen is introduced into the solution.

An angioplasty catheter having a central channel lies in communication with the oxygen-supersaturated physiologic solution, which is infused into the artery without bubble formation.

BEST MODE(S) FOR PRACTICING THE INVENTION

1. The Apparatus

Figure 1:
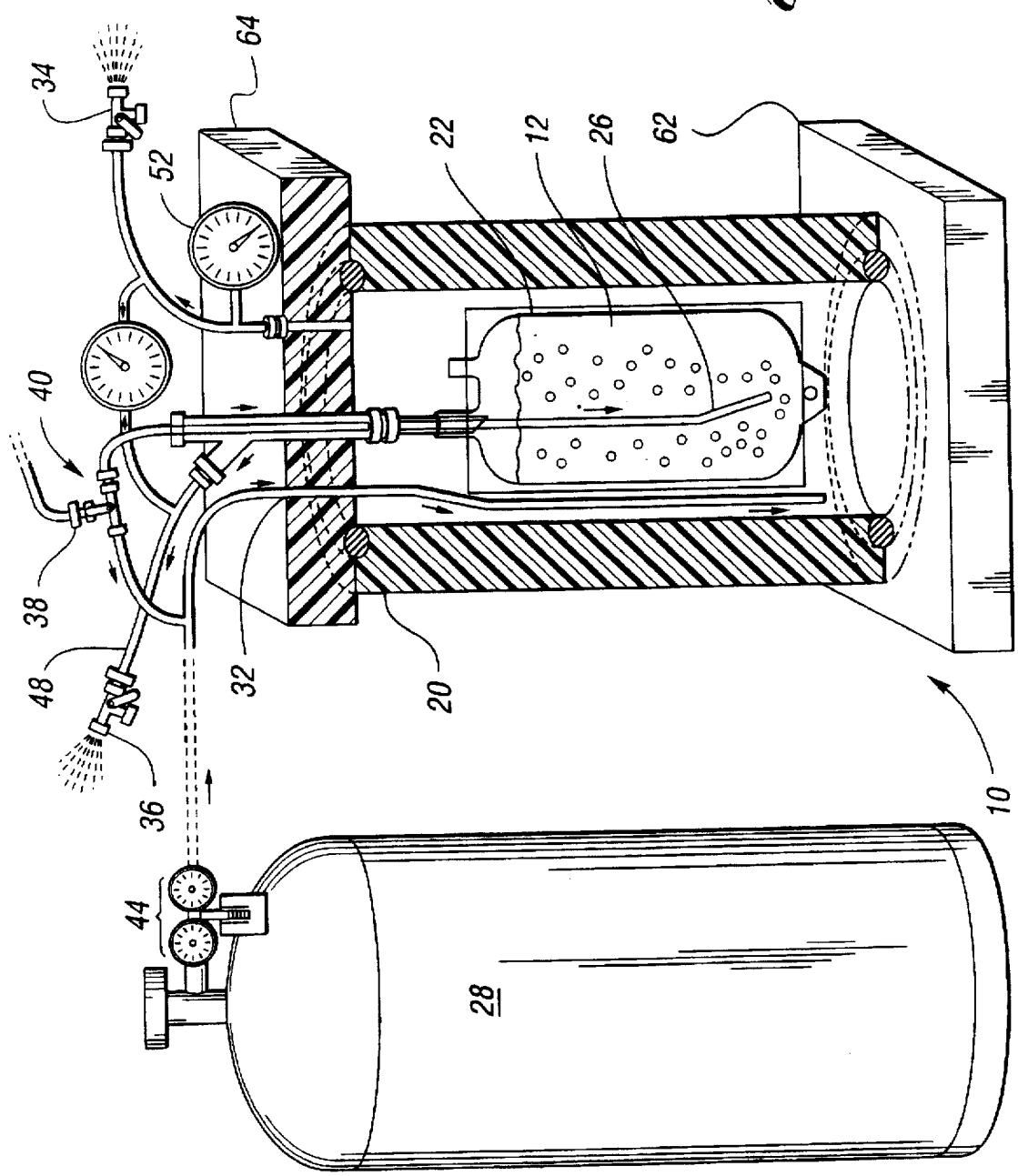
FIG. 1 is a schematic illustration of an apparatus for preparing an oxygen-supersaturated solution.
Figure 2:
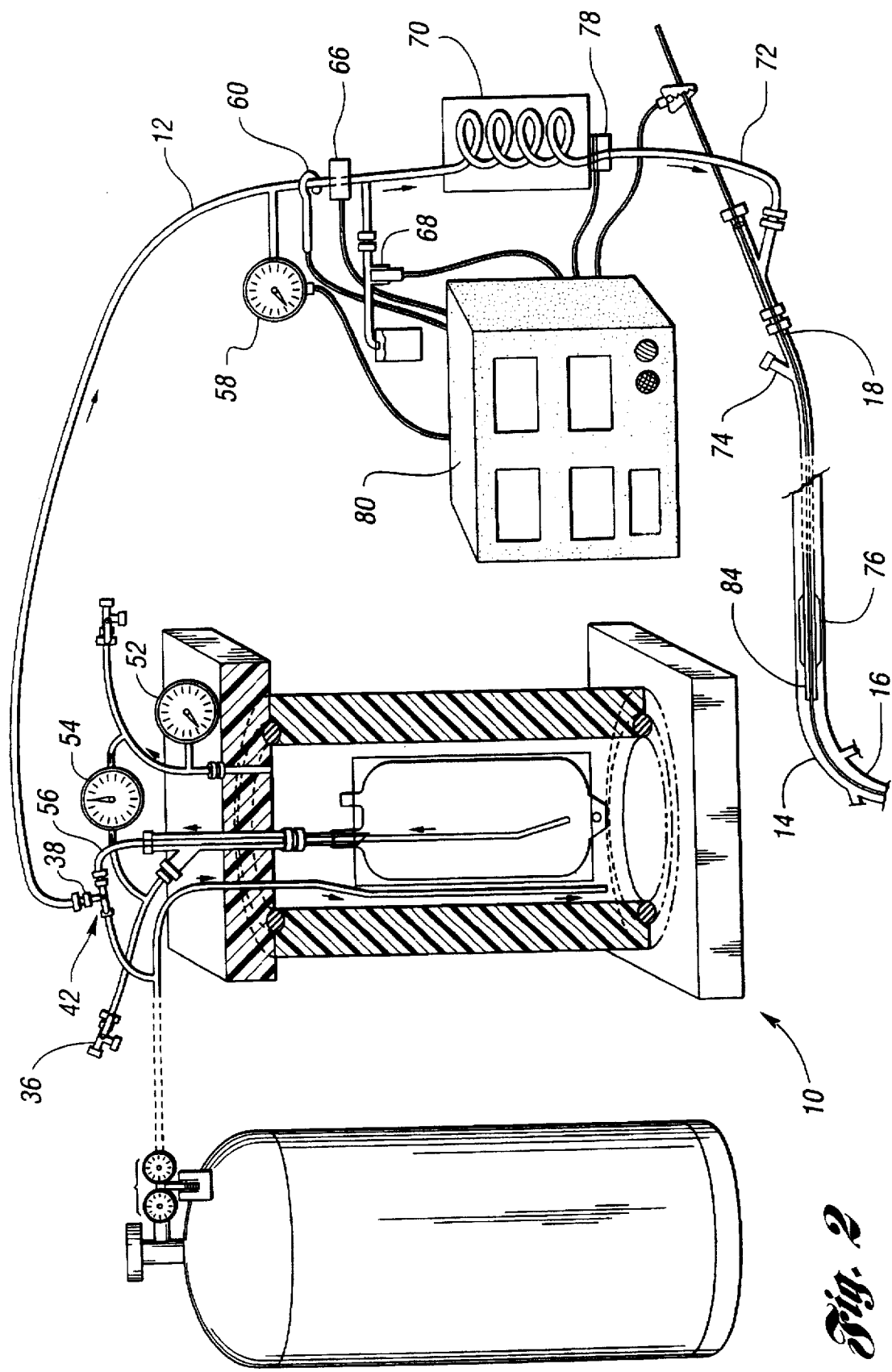
FIG. 2 illustrates a configuration of the apparatus wherein the oxygen-supersaturated solution is delivered to a lumen of a blood vessel to replace arterial blood beyond an angioplasty device.

Turning first to FIGS. 1-2 of the drawing, there is depicted an apparatus 10 for delivering an oxygen-enriched or oxygen-supersaturated physiologic solution 12 into a lumen 14 of a blood vessel 16 to replace arterial blood beyond an angioplasty catheter 18 during clinical angioplasty. The apparatus 10 operates in two modes: (1) preparation of the oxygen-supersaturated solution (FIG. 1); and (2) delivery of the oxygen-supersaturated solution to the angioplasty catheter (FIG. 2).

In FIGS. 1 and 2, there is depicted an apparatus 10 for delivering the oxygen-supersaturated physiologic solution 12 into a lumen 14 of a blood vessel 16 to replace arterial blood beyond an angioplasty catheter 18 during clinical angioplasty. The apparatus 10 includes a hollow, gas-tight vessel 20 within which is disposed a collapsible container 22 of initially oxygen-depleted physiologic solution 12. A space 24 exists between the container 22 and the vessel 20 into which the collapsible container 22 may expand.

A trocar 26 is sealingly inserted into the vessel 20 and the container 22. Within the container 22, a perforated section of the trocar 26 extends below a meniscus of the physiologic solution 12 which occupies the container 22. Upon connection with a supply 28 of oxygen under pressure, the trocar 26 drives the oxygen into the solution, thereby preparing an oxygen-supersaturated solution within the container 22.

An inlet port 32 is provided in the vessel 20 in communication with the space 24 and the supply 28 of oxygen. By the use of suitable valving which will be described in greater detail below, a single supply 28 of oxygen creates a differential in gas pressure across the walls of the container 22 within the gas-tight vessel 20.

Also connected to the vessel 20 in communication with the space 24 is an adjustable space exit valve 34, the valve 34 enabling control to be exercised over the flow of oxygen from the space 24 so that the oxygen may leave the space 24 at a higher rate than that at which oxygen is introduced into the solution.

A fluid control means 38, such as a valve having a T-junction, has a gas-opened state 40 (FIG. 1) in which the oxygen may flow from the supply 28 into the trocar 26. In a gas-closed state 42 (FIG. 2) the oxygen supply 28 is isolated and the oxygen-supersaturated solution flows from the trocar 26 through a delivery tube 56 to the angioplasty catheter 18.

The angioplasty catheter 18 has a central channel 20 in communication with the oxygen-supersaturated physiologic solution 12, which is infused into the blood vessel without bubble formation beyond the angioplasty catheter 18.

The experimental apparatus and procedure depicted in FIG. 1 will now be described in more detail.

The supply 28 of oxygen is typically housed at a pressure at or below about 2500 psi. Near the tank's outlet, an oxygen supply regulator 44 (adjustable resistance) is provided for reduction of supply pressure to about 15–30 psi. Thus, the oxygen pressure inside the vessel 20 and outside the container 22 that occupies the space 24 is of the order of 15–30 psi. Typically, the regulator 44 is provided with gauges or other means which signal the pressure of oxygen supplied to the container 22 and the space 24.

The regulator 44 is connected to a trocar 26 via a tube, which has a branch that leads into the inlet port 32 provided in the vessel 20. Branching from the tube is a section along which oxygen may pass toward a stop cock or other fluid control means 38 which when in a gas-opened state (FIG. 1), allows the oxygen to pass into the trocar 26.

If desired, the trocar 26 may be provided with multiple holes for delivery of the oxygen into solution in the container 22 under pressure. The trocar 26 is also used for ejection of the oxygen-supersaturated solution from the container 22 in a manner to be described below.

Upon entry into the physiologic solution from the trocar 26, oxygen bubbles rise within the oxygen-depleted physiologic solution in the container 22 to become dissolved under pressure therein, thereby to form the oxygen-enriched physiologic solution. The container 22 preferably has a capacity of about 1–2 liters.

If desired, a clear, non-oxygen permeable plastic tape or adhesive sheet (not shown) may be applied to the external surface of the container 22 within the gas-tight vessel 20. The plastic tape or film disposed about the outside of the container 22 tends to prevent oxygen diffusion through the container 22 into solution.

A port may be provided for the injection of ions, drugs, and the like into the container 22 before emplacement of the container 22 within the vessel 20.

To provide an escape path for undissolved oxygen which occupies a volume above the meniscus of physiologic solution and within the container 22, a passage 48 is provided. A container exit valve 36 may be connected thereto for controlling the rate of escape of oxygen venting from the container 22.

The adjustable space exit valve 34 communicates with a pressure sensing means 52 that enables pressure inside the space 24 within the vessel 20 to be monitored. A differential pressure sensing means 54 is provided to signal the pressure difference between oxygen leaving the space 24 and the container 22.

The space exit valve 34 allows oxygen to vent at a higher flow rate from the space 24 than the bubble flow rate within the container. This creates a pressure outside the container in the space that is a few psi below the pressure within the container 22.

A preferable construction of the apparatus of the present invention comprehends the vessel 20 being fabricated from a clear gas-tight material such as an acrylic, or polycarbonate, or the like. Preferably, the vessel is cylindrical for uniformity of pressure distribution. Clear end plates 62,64 seal the vessel 20 so that it is gas-tight. If desired, latches may be provided for retaining the end plates (not shown) in relation to the cylinder.

Turning now to FIG. 2, there will be described in greater detail the apparatus which is used to deliver the oxygen-supersaturated solution that is prepared as illustrated in FIG. 1. The regulator 44 is adjusted so that the outlet pressure from the oxygen supply is within the 20–200 psi range. The valves 36 and 34 are closed to oxygen flow and the fluid control means 38 is in its gas-closed state 42. The pressure differential gauge 54 indicates a reading of about 0 psi, while pressure gauge 52 indicates a pressure in the space 24 to be about 20–200 psi.

The pressure of oxygen (about 20–200 psi) forces the undissolved gas out of the container and provides a hydrostatic pressure to: (a) dissolve all bubbles; and (b) deliver the now oxygen-supersaturated solution at a desired flow rate through the delivery tube 56, which is preferably fabricated from a plastic pressure tubing, or the like.

Various monitoring parameters are derived. If desired, a pressure sensor 58 may be provided in communication with the delivery tube 56. A flow probe 60 may also be provided, as may a bubble detector 66.

A portion of the flow passing along the delivery tube is provided to permit a sample (about 1–5% of mainstream) for siphoning a specimen for analysis. This solution passes through a sensor 68 for detecting the partial pressure of oxygen within the oxygen-supersaturated physiologic solution.

As the delivery tube and its effluents pass through a heat exchanger 70, a thermal equilibrium is attained in which the oxygen-supersaturated physiologic solution is maintained at about 37° before passing along a section of thermally insulated tube 72 and to the central channel of the angioplasty catheter 18.

Conventionally, the angioplasty catheter 18 includes a balloon inflation port 74 and a balloon 76, which is inflated within a blood vessel such as a coronary artery 16. Passage of the oxygen-supersaturated physiologic solution along the central channel of the catheter 18 permits the oxygen-supersaturated solution to fill the lumen 14 of the coronary artery 16 distal to the balloon 76, as shown.

As schematically illustrated in FIG. 2, a monitoring means 80 is provided which senses and displays values for pressure as detected at the pressure sensor 58; flow rate, as detected at the flow probe 60; oxygen partial pressure, as detected at the oxygen pressure sensor 68; an ECG readout via an ECG means 82, and signals (intra coronary) transmitted by the angioplasty guide wire. If desired, an electronic shut-off means 78 is provided, wherein flow is truncated if the monitored parameters fail to lie within acceptable ranges. Conventionally, the monitoring device 80 includes a manual stop button and a start button which opens the electronic shut-off valve 78. Optionally, a timer may be provided wherein the duration of infusion may be set.

2. The Method

During angioplasty catheter operations, when a coronary artery is temporarily occluded during clinical angioplasty, such as during balloon angioplasty, delivery of a physiologic solution, containing oxygen dissolved at 2–3 bar, at a liquid flow rate of 10 to 60 mL/min into the vessel beyond the angioplasty device will greatly reduce or even abolish myocardial ischemia. At such pressures and flow rates, the risk of bubble formation and potential oxygen toxicity is reduced.

Thus, addition of oxygen-supersaturated solutions to flowing arterial blood is performed optimally when a high concentration, on the order of 1–3 mL $O_2$/g, is used, thereby necessitating a low liquid flow rate (1–2 mL/min for an average coronary artery having a blood flow rate of about 100 mL/min) to achieve a net $O_2$/g concentration in the blood of about 2–3 bar.

As shown in FIGS. 1 and 2, the method provides a physiologic solution containing 2–3 bar of dissolved oxygen to a coronary artery during angioplasty in a simple, safe, and effective manner.

The container 22 has a physiologic solution in a volume of about 1 liter of normal saline to which other components, such as potassium, calcium, magnesium ions, glucose, buffers, etc., can be added.

The vessel 20 is, for example, an acrylic cylinder, approximately 6 in. in internal diameter with a wall thickness of about ½ in. It can be pressurized, after sealing the ends with plastic plates 62,64 and o-rings, to greater than 200 psi.

Prior to placement in the vessel, the surface of the bag may be covered with a translucent plastic film which is relatively impermeable to oxygen. For example, application of clear packaging tape to the outside surface of the bag is effective for this purpose.

After placement of the bag 22 in the vessel 20, a dip trocar or trocar 26 within the bag is used to bubble oxygen at a target partial pressure, on the order of 2–3 bar. The space 24 external to the container is pressurized by the same oxygen source that pressurizes the trocar 26. Allowing oxygen to leak at a slightly faster flow rate from the space outside the bag compared to the bubble flow rate ensures that a differential pressure of a few psi is obtained which permits the flow of oxygen through the trocar 26 at an appropriate rate.

Once the solution in the bag 22 has reached the target partial pressure of oxygen, flow through the dip trocar 26 is stopped and the oxygen pressure external to the bag is increased slightly to drive out any pockets at the top of the bag. The same source of oxygen is then used to increase the oxygen pressure in the vessel 20 to provide hydrostatic pressure for achieving liquid flow rates required for the coronary artery application.

For example, pressures of about 30 to 60 psi can be used to deliver the oxygen supersaturated liquid at about 35 to 70 mL/min through the central channel of an angioplasty catheter without the presence of a guide wire. Pressures of 50–150 psi can be used to deliver the same flow rates when a guide wire is left in the central channel of the angioplasty catheter.

The hydrostatic pressure serves not only to drive the solution at an appropriate flow rate, but also forces any oxygen bubbles into solution, so that no bubbles are delivered into the artery.

Additional hydrostatic pressure can be applied to the oxygen-enriched fluid after it leaves the bag, so that a sufficiently high pressure can be achieved proximal to high resistance (such as a hollow guide wire, or small silicon capillary tube) encountered in an exit channel. The additional hydrostatic pressure could be applied by one or a variety of water pumps, such as an air-driven water pump.

The relatively small channel (0.020" or smaller in most PTCA catheters) within the angioplasty catheter for delivery of the solution provides flow resistance means 84 a suitably high resistance which stabilizes the meniscus solution during infusion into a blood vessel.

As is apparent from the above description, a small tank of oxygen can be used to both oxygenate a physiologic solution and provide the hydrostatic pressure for delivering the solution through the catheter.

Maintenance of sterility of the solution is simple with this system, since all tubing and fittings can be made inexpensively and, therefore, are disposable after use.

A few additional features can be added to the tubing at the outlet of the system to control the parameters of interest. Both pressure and flow can be monitored continuously and $PO_2$ can be monitored either from a side port or in a small tributary or side stream siphoned from the delivery tubing. Should pressure, flow, or $PO_2$ fall outside of expected limits, the flow could be stopped with automatic electronic controls.

By monitoring the ECG from the distal end of a standard guide wire within the angioplasty catheter, for example, with an alligator clip connected to a "V" lead of a 12 lead ECG machine, intra-cardiac electrical activity can be used to determine if bubbles are produced inadvertently.

Electrical impedance in blood is greatly reduced by the presence of gas bubbles, as I recently observed in an in vivo dog study. Even a few bubbles in a coronary artery, at a level which can be tolerated for a few minutes without sequelae, reduce the ECG signal from >20 mV to 0 within 2 seconds.

The automatic shutoff mechanism 78 is incorporated in the oxygen-supersaturated solution delivery system. It is based on sensing a fall in the intra-cardiac ECG signal as monitored from the angioplasty guide wire. Thus, the delivery system is highly safe and reliable.

A similar delivery system could easily be employed for providing cardioplegia solutions for protection of the myocardium during cardio-pulmonary surgical procedures. In that environment, a catheter would be inserted typically in the aortic root for intermittent delivery of either cold or warm cardioplegia solution which is supersaturated with oxygen, typically at about 2–3 bar dissolved oxygen pressure.

The improved oxygen delivery afforded by the oxygen-enriched cardioplegia solution would reduce injury to the myocardium as a result of reperfusion upon completion of cardio-pulmonary bypass. As a result, myocardium performance would be enhanced, compared to the use of cardioplegia solutions which are not enriched with oxygen.

The artery of interest is not restricted to the coronary. It could be any artery in the body for delivering the oxygen-supersaturated fluid, such as cerebral arteries or for treatment of patients with a stroke or for arteries that supply tumors for enhancing radiation therapy of tumors with the oxygen-enriched fluid.

The oxygen-enriched fluid can be delivered to any appropriate catheter that stabilizes the fluid during delivery.

Having above indicated a preferred embodiment of the present invention, it will occur to those skilled in the art that modifications and alternatives can be practiced within the spirit of the invention. It is accordingly intended to define the scope of the invention only as indicated in the following claims.

We claim:

1. An apparatus for delivering a gas-supersaturated solution to a delivery site comprising:

a hollow, gas-tight vessel;

a collapsible container of solution disposed within the vessel so that a space between the container and the vessel is provided;

a tubular member sealingly inserted into the vessel and the container, the tubular member being in communication with a supply of gas under pressure for driving the gas into the solution via the tubular member, thereby preparing gas-supersaturated solution within the container;

an inlet port provided in the vessel in communication with the space and the supply of gas for pressurizing the space;

an adjustable container exit valve in communication with the container, the container exit valve controlling the flow of undissolved gas from the container;

an adjustable space exit valve in communication with the vessel, the space exit valve capable of controlling the flow of gas from the space so that gas leaves the space at a higher rate than that at which gas is introduced into the solution;

a fluid control means having a gas-opened state which permits the gas to flow from the supply into the tubular member and a gas-closed state which precludes the gas from flowing from the supply to the tubular member by the fluid control means and the gas-supersaturated solution may flow from the tubular member to the delivery site without bubble formation.

2. The apparatus of claim 1, further comprising:
an gas-impermeable sheet applied to an external surface of the container.

3. The apparatus of claim 1, further comprising:
a port provided within the container for injecting ions, drugs, and the like into the container before emplacement of the container within the vessel.

4. The apparatus of claim 1, wherein the container exit valve provides an escape path for undissolved gas.

5. The apparatus of claim 1, wherein the space exit valve permits pressure inside the space to be regulated so that a pressure differential is created between gas leaving the space and the container whereby a pressure outside the container in the space is less than the pressure within the container.

6. The apparatus of claim 1, wherein the vessel is cylindrical.

7. The apparatus of claim 1, wherein the gas is oxygen.

8. The apparatus of claim 1, wherein the solution comprises:
a saline solution.

9. The apparatus of claim 8, further comprising an additive to the saline solution, the additive being selected from the group consisting of potassium, calcium, magnesium ions, glucose, buffers, and mixtures thereof.

10. The apparatus of claim 1, further comprising:
a delivery tube with a first end connected to the tubular member and a second end disposed toward the delivery site for delivering the gas-supersaturated solution to the delivery site.

11. The apparatus of claim 10, further comprising:
a pressure sensor in communication with the delivery tube for sensing the pressure of the gas-supersaturated solution in the delivery tube.

12. The apparatus of claim 10, further comprising:
a flow probe in communication with the delivery tube which measures the flow rate of the gas-supersaturated solution in the delivery tube.

13. The apparatus of claim 10, further comprising:
a bubble detector in communication with the delivery tube for detecting bubbles in the gas-supersaturated solution in the delivery tube.

14. The apparatus of claim 10, further comprising:
a sensor in communication with the delivery tube for detecting the partial pressure of gas within the gas solution in the delivery tube.

15. The apparatus of claim 10, further comprising:
a heat exchanger disposed at the second end of the delivery tube for creating and maintaining a temperature in the gas-supersaturated solution of about 37° C. before delivery to the delivery site.

16. The apparatus of claim 15, further comprising:
a thermally insulated section of tubing connected to the heat exchanger.

17. The apparatus of claim 16, further comprising:
a safety valve in communication with the thermally insulated section whereby flow of the gas-supersaturated solution from the heat exchanger is shut off if monitored parameters are not in an acceptable range.

18. The apparatus of claim 17, further comprising:
an angioplasty catheter connected to the thermally insulated section of tubing for infusing the gas-supersaturated solution into a blood vessel, said catheter including a guidewire; and
means for generating an ECG signal connected to the guide wire, based on intra-coronary observation.

19. The apparatus of claim 18, further comprising:
a flow resistance means disposed within the angioplasty catheter, whereby a suitably high resistance is afforded which stabilizes the gas-supersaturated solution during infusion into the blood vessel.

20. An apparatus for producing and delivering a gas-enriched solution comprising:
a pressurizable housing having an input and an output;
a collapsible container containing a solution and disposed within the housing, wherein the housing and the container forms a space therebetween, said space containing a first pressurized gas;
an input tubular member in communication with the housing input, wherein the input tubular member extends into the solution for delivering a second pressurized gas to the solution, thereby preparing a gas-enriched solution within the container; and
an output tubular member in communication with the housing output, wherein the output tubular member extends into the container for allowing undissolved gas to exit from the container and wherein the output tubular member further extends into the solution for delivering the gas-enriched solution.

21. The apparatus of claim 20, wherein the container comprises a port for injecting a substance into the container before emplacement of the container within the housing.

22. The apparatus of claim 20, further comprising a valve in communication with the housing output for regulating the flow of the undissolved gas from the container.

23. The apparatus of claim 20, wherein the housing is cylindrical.

24. The apparatus of claim 20, further comprising a delivery tube connected to the housing output for delivery of the solution to a delivery site.

25. A method for delivering a gas-supersaturated solution to a delivery site, comprising:
placing a collapsible container of a solution within a hollow, gas-tight vessel so that a space between the container and the vessel is provided;
locating a tubular member within the container, the tubular member being in communication with a supply of gas under pressure;
dissolving the gas into the solution under pressure to prepare the gas-supersaturated solution within the container;
controlling respective gas flow rates into the solution and from the space so that the gas leaves the space at a higher rate than that at which gas is introduced into the solution; and
delivering the gas-supersaturated solution to the delivery site.

26. The method of claim 25, further comprising:
arresting flow of gas through the tubular member when the gas-supersaturated solution has reached a target partial pressure of gas;
increasing the gas pressure within the space to drive out any pockets lying above a meniscus of the solution within the container; and
increasing gas pressure in the space to provide hydrostatic pressure for achieving liquid flow rates required for coronary artery applications.

27. The method of claim 25, wherein the step of delivering the gas-supersaturated solution comprises:
infusing the solution under a pressure of about 2–3 bar at a liquid flow rate of about 10–16 mL/min.

28. The method of claim 27, wherein the step of delivering the gas-supersaturated solution comprises:
infusing the solution at a concentration of about 1–3 mL $O_2$/g.

29. The method of claim 28, further comprising:
supplementing the solution within the container with an additive selected from the group consisting of potassium, calcium, magnesium ions, glucose, buffers, and mixtures thereof.

30. A method for creating a gas-enriched solution and delivering the solution to a delivery site, comprising the steps of:
providing a collapsible container containing a solution in a housing with an input and an output such that a space is created between the container and the housing, wherein the space contains a gas;
providing an output tubular member within the container and in communication with the housing output and extending at least a portion of the output tubular member into the solution;
pressurizing the gas in the space;
delivering a pressurized gas into the solution through the input tubular member thereby creating the gas-enriched solution; and
delivering the gas-enriched solution to the delivery site through the housing output via the output tubular member.

31. The method of claim 30, wherein the step of delivering the gas-enriched solution comprises infusing the solution under a pressure of about 2–3 bar and at a liquid flow rate of about 10–16 mL/min.

32. The method of claim 30, further comprising the steps of:
terminating the delivery of the pressurized gas into the solution when the gas-enriched solution has reached a predetermined gas partial pressure;
providing a first gas pressure within the space to expel undissolved gas from within the container through the housing output via the output tubular member; and
providing a second gas pressure within the space to deliver the gas-enriched solution through the housing output via the output tubular member to the delivery site at a predetermined flow rate.

* * * * *